ate of Patent:

United States Patent [19]

DeGraff et al.

[11] Patent Number: 5,336,821
[45] Date of Patent: Aug. 9, 1994

[54] ALKYLATION PROCESS WITH REACTOR EFFLUENT HEAT RECOVERY

[75] Inventors: Richard R. DeGraff, Deerfield; Peter J. Van Opdorp, Naperville; Russell C. Schulz, Darien, all of Ill.

[73] Assignee: UOP, Des Plaines, Ill.

[21] Appl. No.: 57,397

[22] Filed: May 6, 1993

[51] Int. Cl.$^5$ .......................... C07C 15/02; C07C 5/09; C07C 2/64
[52] U.S. Cl. ................................ 585/402; 585/435; 585/449; 585/450; 585/910
[58] Field of Search ............... 585/402, 435, 449, 450, 585/910

[56] References Cited

U.S. PATENT DOCUMENTS

| | | | |
|---|---|---|---|
| 4,008,290 | 2/1977 | Ward | 260/672 T |
| 4,051,191 | 9/1977 | Ward | 260/671 R |
| 4,587,370 | 5/1986 | DeGraff | 585/450 |
| 4,695,665 | 9/1987 | De Graff | 585/450 |
| 4,885,424 | 12/1989 | Ferk et al. | 585/450 |

*Primary Examiner*—Anthony McFarlane
*Assistant Examiner*—Nhat D. Phan
*Attorney, Agent, or Firm*—Thomas K. McBride; John G. Tolomei

[57] ABSTRACT

A process for the alkylation of aromatic hydrocarbons such as cumene and ethylbenzene is disclosed. A portion of the effluent stream from an alkylation reactor passes through an indirect heat exchanger to transfer heat to a flashed stream containing the product aromatic hydrocarbons. The heat exchanger recovers the exothermic heat of reaction from the effluent stream for use elsewhere in the process. This method of heat exchange is especially useful in alkylation processes where the temperature of the effluent stream is relatively low, such as where the alkylation reactor contains a zeolite catalyst.

11 Claims, 1 Drawing Sheet

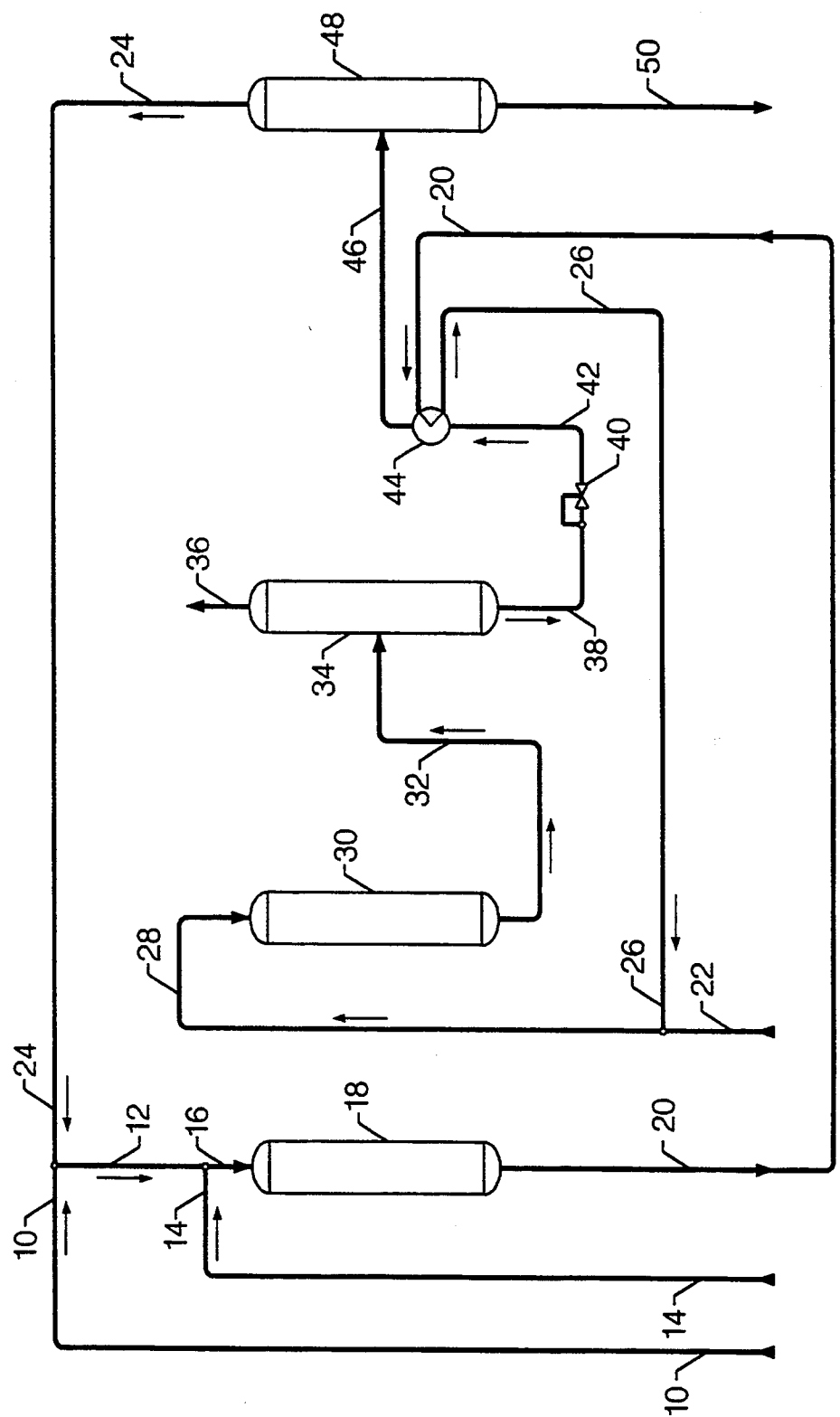

ALKYLATION PROCESS WITH REACTOR EFFLUENT HEAT RECOVERY

FIELD OF THE INVENTION

The invention relates to a hydrocarbon conversion process. The invention relates generally to an improved process for the alkylation of aromatic hydrocarbons. The invention more specifically relates to an indirect heat exchange method to transfer heat from an effluent of an alkylation reactor using a zeolite catalyst.

BACKGROUND OF THE INVENTION

The present invention is broadly applicable to the production of alkylated hydrocarbons. These compounds are useful in themselves and more frequently in subsequent chemical synthesis of other compounds. The present invention is particularly applicable to the production of cumene, or isopropylbenzene. Another application of the present invention is in the production of ethylbenzene.

Many industrial alkylation processes use a Friedel-Crafts type of catalyst such as aluminum chloride or solid phosphoric acid (SPA). These catalysts are corrosive and may be difficult to dispose of. By contrast, zeolite catalysts are less corrosive and not as difficult to dispose of, and so zeolite catalysts have replaced Friedel-Crafts type catalysts in some commercial processes. Zeolite catalysts are also advantageous because generally they catalyze the alkylation of aromatics at lower reaction temperatures than Friedel-Crafts catalysts. Although this characteristic is usually an advantage from a catalytic viewpoint, it can also be a disadvantage from an energy-utilization viewpoint. This is because a lower reaction temperature generally also means that the temperature of the reactor effluent is lower too, and therefore the options for using the energy of the effluent elsewhere in the process are more limited. This is a specific illustration of a more general characteristic of energy utilization, namely that it is usually more difficult to utilize the "low grade" or waste heat in a stream that is at a relatively low temperature than it is to utilize the "high grade" heat in a stream at relatively high temperature.

In alkylation processes, for example, the "high grade" heat in the reactor effluent of prior art processes that use Friedel-Crafts catalysts is generally and most conveniently used in the rectifier to separate some of the unreacted aromatic from the effluent for recycle to the reactor U.S. Pat. No. 4,051,191 issued to Ward discloses such a process. In contrast, the heat in the reactor effluent of processes that use zeolite catalysts is "low grade" and generally is insufficient to recover much of the unreacted aromatic unless more energy is supplied to either the effluent itself or the depropanizer. For this reason, the waste heat of the effluent of related art processes that use zeolite catalysts is used in low temperature heating applications, such as preheating cold feed to the alkylation reactor. U.S. Pat. No. 4,008,290 issued to Ward discloses such a process in which alkylation reactor feed is heated by recycling a portion of the alkylation effluent. Alternatively, the waste heat is used in waste heat boilers to produce low pressure steam. However, since it is common generally in hydrocarbon processing and particularly in alkylation processes that there is an abundance of such low pressure steam already, it is more efficient and economical to use this waste heat in some other useful way.

This invention utilizes the heat of reaction in a more effective manner than the prior art processes that use a depropanizing zone, such as the process disclosed in U.S. Pat. No. 4,587,370. In such prior art processes, the bottoms stream from the depropanizing zone passes into a benzene column which removes benzene that is recycled to the alkylation reactor. Since the benzene column generally operates at a lower pressure than the depropanizing zone which feeds it, the depropanizing zone bottoms stream generally passes through a pressure control valve before entering the benzene column. Despite this pressure decrease, a relatively small portion of the depropanizing zone bottoms stream vaporizes, and a substantial portion of the depropanizing zone bottoms stream, including benzene and mono- and polyalkylated aromatic hydrocarbons, remain in the liquid phase. In the prior art processes, the temperature decrease, if any, that occurs when the depropanizing zone bottoms stream passes through the pressure control valve is not used for recovering heat to help separate the hydrocarbons in the stream.

BRIEF SUMMARY OF THE INVENTION

The present invention provides a process for indirectly exchanging heat with at least a portion of an effluent stream from an alkylation reactor. The process exchanges the waste heat in the effluent stream with a flashed stream from another section of the process. This utilizes the exothermic heat of reaction o in a particularly efficient manner.

This invention is a novel and particularly effective method of recovering the waste heat from the effluent stream of an alkylation reactor, particularly when the temperature of the effluent stream is relatively low. Using indirect heat exchange, the waste heat may be recovered from the net effluent stream of the reaction section, as well as from a reactor effluent recycle stream. Unlike the related art processes that use much of this waste heat to make low pressure steam, this invention integrates this waste heat into the process to help separate unreacted aromatics from the alkylaromatic product. In practicing this invention in the production of cumene, this waste heat will be exchanged from the reactor effluent to the flashed depropanizer bottoms stream.

In the present invention, the temperature of the flashed depropanizer bottoms stream is below the temperature of the reactor effluent. Thus, although as described above the temperature of the reactor effluent stream is relatively low, the temperature of the flashed depropanizer bottoms stream is lower than that of the reactor effluent stream. Flashing the depropanizer bottoms stream lowers not only the pressure but also the temperature of the depropanizer bottoms stream to a temperature that is low enough to exchange heat indirectly with the reactor effluent stream, yet still high enough that the heat exchanged from the effluent stream will vaporize benzene in the flashed depropanizer bottoms stream when the effluent stream is exchanged indirectly with the reactor effluent. In this way, the waste heat from the reactor effluent is used to provide part of the heat required to separate unreacted benzene from the cumene product.

In the production of cumene, for example, vaporizing the unreacted benzene in the depropanizer bottoms stream is an especially advantageous use of the waste heat from the effluent stream. This invention adds heat to the depropanizer bottoms stream which assists in the separation of benzene and cumene in the benzene column immediately downstream. Since the function of the benzene column is to perform this benzene/cumene separation, this invention decreases the design requirements of the benzene column, thereby decreasing its capital and operating costs. Since the cost of recovering cumene is a significant proportion of the total cost of producing cumene, this invention is a more economical use of the waste heat.

One broad embodiment is a process for indirectly exchanging heat with at least a portion of an effluent stream from a first alkylation zone. Some of the first alkylation zone's effluent stream which comprises alkylaromatic hydrocarbons exchanges heat in a means for indirect heat exchange. After heat exchanging, some of the first effluent stream passes into either a second alkylation zone or a first separation zone or both, to produce a second effluent stream comprising alkylaromatic hydrocarbons. Some of the second effluent stream flashes. After flashing, some of the second effluent stream exchanges heat in the means for indirect heat exchange. After heat exchanging, alkylaromatic hydrocarbons are recovered from some of the second effluent stream in a second separation zone.

Another embodiment is a process for alkylating aromatic hydrocarbons. At least one aromatic hydrocarbon is alkylated with at least one addition compound in a first alkylation zone to produce a first effluent stream comprising alkylaromatic hydrocarbons. A first portion of the first effluent stream passes into either a second alkylation zone or a first separation zone or both, to produce a second effluent stream comprising alkylaromatic hydrocarbons. Some of the second effluent stream flashes. After flashing, some of the second effluent stream exchanges heat in a means for indirect heat exchange. A second portion of the first effluent stream exchanges heat in the means for indirect heat exchange, and, after heat exchanging, some of the second portion of the first effluent stream recycles to the first alkylation zone. After heat exchanging, alkylaromatic hydrocarbons are recovered from some of the second effluent stream in a second separation zone.

Although this invention is particularly useful for alkylation processes that employ zeolite catalysts, it is not limited to zeolite catalysts. It can be used for alkylation processes employing other catalysts that have a relatively low reactor effluent temperature.

Other embodiments, purposes, and objectives will become clear from the ensuing discussion.

BRIEF DESCRIPTION OF THE DRAWING

FIG. 1 is a simplified process flow diagram of an embodiment of the invention.

DETAILED DESCRIPTION OF THE INVENTION

The feed hydrocarbons charged to the subject process are an aromatic hydrocarbon and an addition compound. The aromatic hydrocarbons include benzene, toluene, xylenes, ethylbenzene, normal propyl benzene, isopropylbenzene, and other aromatic ring compounds. Higher molecular weight and polycyclic aromatic hydrocarbons may also be used. The addition compound may be an olefin-acting compound such as an alcohol, ether, or ester including alkyl halides, alkyl sulfates and alkyl phosphates. Preferably, the addition compound is an alkylating agent such as a mono- or di-olefin having from 2 to 8 carbon atoms per molecule. The preferred mono-olefins include ethylene, propylene, 1-butene, 2-butene, and isobutylene. These olefins may be used as relatively pure streams containing a single hydrocarbon species. Alternatively, a mixture of two or more olefins or of olefins and paraffins having from 2 to 8 carbon atoms per molecule may be used as the non-aromatic feed stream to the process. Typical products include cumene, ethylbenzene and cymene (isopropyl toluene).

The most widely practiced hydrocarbon conversion process to which the present invention is applicable is the catalytic alkylation of benzene with propylene to produce cumene. Therefore, the discussion herein of the present invention will be in reference to its application to a catalytic cumene reaction system. It is not intended that this discussion limit the scope of the present invention as set forth in the claims.

A feed stream containing propylene and another stream containing benzene in stoichiometric excess to propylene pass into an alkylation reactor containing an alkylation catalyst. Generally, the feed to the reactor is in a liquid phase, at a temperature between 150° and 250° C., and at a pressure between 28 and 70 atmospheres. Although the catalyst may move through the reactor in a moving bed, more typically the catalyst is in the reactor in a fixed bed. The reactions that produce cumene are principally exothermic, and so the temperature of the reaction mixture rises as it passes through the alkylation reactor. Although some cumene reactors have indirect heat exchange means to remove the heat as it is produced, most cumene reactors are adiabatic. Thus, the heat produced in the reactor exits with the effluent stream, and the outlet temperature of the effluent stream is higher than the inlet temperature of the reactants. The temperature rise from the inlet to the outlet of the alkylation reactor may be from about 10° to about 190° C., depending on the total mass flows in the reactor. The space velocity of olefin may range from about 0.01 to about 0.05 gram-mole of olefin per gram of catalyst per hour. It is preferred that an excess of benzene be present in the reaction zone. The mole ratio of benzene to the olefin should be within the broad range of 3:1 to 50:1. A ratio of about 25:1 is preferred for the production of cumene. Under these conditions, the temperature rise from the inlet to the outlet of the alkylation reactor is from about 5° to about 100° C.

The effluent stream contains cumene. It may also contain other mono-and poly-alkylated aromatic hydrocarbons. It generally contains benzene, unreacted paraffins such as propane that were present in the propylene-containing feed stream, as well as some unreacted propylene. The effluent stream may pass into a means for indirect heat exchange for the purpose of transferring a portion of the heat of reaction from the effluent stream, thereby cooling the effluent stream.

The cooled effluent stream may then pass into either a second alkylation reaction zone or a separation zone. Where the effluent stream passes into a second alkylation zone, the effluent stream may be cooled to a temperature so that the feed stream to the second reaction zone is below the temperature of the outlet of the first reactor. Preferably the temperature of the feed stream to the second reactor is the same as the temperature of the feed to the first reactor.

Where the effluent stream passes into a separation zone such as a depropanizer, the effluent stream may be cooled to a temperature that is suitable for the feed to the separation zone. The suitable temperature of the feed to the separation zone will depend on a variety of factors. Where the separation zone is a distillation column, these factors will include the degree of separation of components to be achieved in the column, the relative rates of product streams withdrawn from the column, the location of the feed point in the column, the size of the reboiler, etc.

The present invention is also applicable to variants on the above flow schemes. Instead of a two-reactor flow scheme, some alkylation processes consist of multiple reaction zones or stages through which the reactants flow in series or in parallel flow. Therefore, in accord with this invention, the effluent from any such reactor in such a flow scheme may be passed through a means for indirect heat exchange prior to passing into another reactor or into a separation zone of the process. Also, instead of once-through flow of reactants through a reactor, some alkylation processes recycle a reactor's effluent back to its inlet or back to the inlet of another reactor in the process. Therefore, in accord with this invention, the effluent from any such reactor in such a flow scheme may be passed through a means for indirect heat exchange prior to recycling it to a reactor in the process. Where the effluent stream is recycled, the effluent stream may be cooled to a temperature below, the same as, or above the desired inlet temperature of the reactor to which it is recycled. The temperature of the combined stream comprising the recycled effluent stream, the feed stream, and any other streams charged to the reactor is preferably the desired inlet temperature of the reactor to which the effluent stream is recycled.

The means for indirect heat exchange is not believed to be critical to the success of this invention. Suitable means for indirect heat exchange can be one of a variety of heat exchangers known to those skilled in the art of hydrocarbon processing. These include shell-and-tube exchangers, exchangers with double-pipe and multi-tube sections, plate-type exchangers, bayonet-tube exchangers, falling film exchangers, and evaporators. Suitable heat transfer equipment is described in Section 11 in *Perry's Chemical Engineers' Handbook*, 6th Edition, McGraw-Hill, N.Y., 1984.

Where the separation zone is a depropanizer distillation column, the column removes the propane from the remainder of the reactor effluent stream. Since the depropanizer column generally operates at a lower pressure than the alkylation reactor which feeds it, the effluent stream generally passes through a pressure control valve before entering the depropanizer. As a result of this pressure decrease, the propane, propylene, and other light hydrocarbons in the reactor effluent may vaporize. However, the vaporized components are a o relatively small portion of the total effluent stream, and a substantial portion of the effluent stream, including the cumene, and any benzene and other mono- and poly-alkylated aromatic hydrocarbons in the reactor effluent, remains in the liquid phase. Consequently, the temperature of the feed stream to the depropanizer is generally only a few degrees below the temperature of the effluent stream. However, a larger temperature drop may be effected by a larger pressure drop of the feed stream across the pressure control valve on the inlet of the depropanizer.

The depropanizer column produces an overhead stream which generally comprises propane, possibly a slight amount of propylene, and other light hydrocarbons and a bottoms stream, which comprises benzene, cumene and may also comprise other mono- and poly-alkylated aromatic hydrocarbons. The bottoms stream is generally a liquid phase stream, at a temperature between about 200° and about 250° C., and at a pressure between about 13 and about 28 atmospheres. The flashed depropanizer bottoms stream is generally a two-phase mixture, at a temperature between about 100° and about 200° C., and at a pressure between about 1 and about 7 atmospheres. The temperature difference between the flashed depropanizer bottoms stream and the reactor effluent stream is generally between about 30° and about 50° C. After the flash, the depropanizer bottoms stream passes into the means for indirect heat exchange to exchange heat with the effluent stream. As a result, the effluent stream is cooled and its temperature decreases, while the flashed depropanizer bottoms stream is heated, a substantial portion of the benzene in the flashed depropanizer bottoms stream vaporizes, and its temperature may increase.

The heated depropanizer bottoms stream may pass on to a downstream section for product recovery. Such a downstream section typically includes a distillation column for separating the recycle benzene from the remainder of the depropanizer bottoms stream. It may also include another distillation column for separating the recycle benzene column bottoms stream into a stream comprising cumene and a stream comprising other mono- and poly-alkylated aromatic hydrocarbons.

The catalyst for the present invention may be one of a broad class of aluminosilicate molecular sieves known as zeolites. The zeolitic molecular sieves suitable for use in the present invention are crystalline aluminosilicates which in the calcined form may be represented by the general formula:

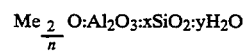

$$Me_{\frac{2}{n}}O:Al_2O_3:xSiO_2:yH_2O$$

where Me is a cation, n is the valence of the cation, x has a value of from about 5 to 100, and y has a value of from about 2 to 10.

Typical well known zeolites which may be used include Zeolite X, Zeolite Y, Linde Type L, medium pore ZSM-type zeolites such as ZSM-5, mordenite, omega, and beta. Detailed descriptions of the above-identified zeolites, as well as others, may be found in D. W. Breck, *Zeolite Molecular Sieves*, John Wiley and Sons, New York 1974, and in other standard references. Preferred zeolites for use in the present invention are rare earth exchanged Y and steam stabilized Y zeolites as disclosed in U.S. Pat. No. 4,459,426 and zeolite beta as disclosed in U.S. Pat. No. 5,081,323.

The Drawing illustrates an embodiment of the invention. For clarity and simplicity, some items associated with the operation of the process have not been shown. These items include flow and pressure control valves, pumps, heat exchangers, temperature and pressure monitoring systems, reactor and fractionator internals, etc., which may be of customary design. This representation of an embodiment is not intended to limit the scope of the present invention in any way.

Referring now to the Drawing, a feed stream comprising a mixture of propane and propylene enters the process in a line 14 and is admixed with a stream of recycle benzene and additional benzene from a line 12. This produces an alkylation zone feed stream carried by a line 16. This stream may be heated in a heat exchanger or a heater, which is not shown, and enters a first reactor 18. The feed stream contacts a zeolite catalyst maintained at alkylation-promoting conditions to effect the reaction of at least a major portion of the propylene with benzene to form cumene. A first reactor effluent stream comprising benzene, propane, cumene, and poly-alkylated aromatic hydrocarbons exits the first reactor 18 in a line 20.

The first reactor effluent stream enters a heat exchanger 44. In the heat exchanger 44, the first reactor effluent stream exchanges heat indirectly with a flashed depropanizer bottoms stream from a line 42. The cooled first reactor effluent stream passes through a line 26 and is admixed with a mixture of propane and propylene that enters the process in a line 22. This produces an alkylation zone feed stream carried by a line 28. This stream may be heated in a heat exchanger or a heater, which is not shown, and enters a second reactor 30. The feed stream contacts a zeolite catalyst maintained at alkylation-promoting conditions to effect the reaction of at least a major portion of the propylene with benzene to form cumene. A second reactor effluent stream comprising benzene, cumene, and poly-alkylated hydrocarbons exits the second reactor 30 in a line The second reactor effluent stream enters a depropanizer 34. The depropanizer 34 separates the effluent stream by distillation into two streams. An overhead stream comprising propane exits the depropanizer 34 in a line 36 and is recovered from the process. A bottoms stream comprising benzene, cumene, and poly-alkylated hydrocarbons exits the depropanizer 34 in a line 38. The depropanizer bottoms stream enters a pressure control valve 40 that reduces not only the pressure but also the temperature of the depropanizer bottoms stream to a temperature that is below the temperature of the first reactor effluent stream. The flashed depropanizer bottoms stream passes through a line 42 into the heat exchanger 44. In the heat exchanger 44, a substantial portion of the benzene in the flashed depropanizer bottoms stream is vaporized by the exchange of heat from the first reactor effluent stream.

The heated, flashed depropanizer bottoms stream passes through a line 46 into a benzene column 48. The benzene column 48 separates the heated, flashed depropanizer bottoms stream by distillation into two streams. An overhead stream comprising benzene exits the benzene column 48 in a line 24, is combined with additional benzene from a line 10, and is sent to the first reactor. A bottoms stream comprising the product cumene and poly-alkylated hydrocarbons exits the benzene column 48 in a line 50, and is recovered from the process.

What is claimed is:

1. A process for indirectly exchanging heat with at least a portion of an effluent stream from an alkylation zone comprising alkylaromatic hydrocarbons which comprises the steps of:
   a. heat exchanging in a means for indirect heat exchange at least a portion of a first effluent stream comprising alkylaromatic hydrocarbons from a first alkylation zone;
   b. passing at least a portion of said first effluent stream after heat exchanging into a second alkylation zone or a first separation zone and recovering therefrom a second effluent stream comprising alkylaromatic hydrocarbons and having a molecular weight that is greater than the molecular weight of said first effluent stream;
   c. flashing at least a portion of said second effluent stream;
   d. heat exchanging in said means for indirect heat exchange at least a portion of said second effluent stream after flashing; and
   e. recovering alkylaromatic hydrocarbons in a second separation zone from at least a portion of said second effluent stream after heat exchanging.

2. The process of claim 1 further characterized in that after heat exchanging, at least a portion of said first effluent stream is recycled to said first alkylation zone.

3. The process of claim 1 further characterized in that a $C_2$–$C_5$ olefin and an aromatic hydrocarbon react to produce alkylaromatic hydrocarbons in said first alkylation zone.

4. The process of claim 3 further characterized in that said first effluent stream further comprises a $C_2$–$C_5$ hydrocarbon and after heat exchanging, at least a portion of said first effluent stream passes into said first separation zone to separate the entering hydrocarbons and to produce an overhead stream comprising $C_2$–$C_5$ hydrocarbons and said second effluent stream, and said overhead stream is rejected from said process.

5. The process of claim 3 further characterized in that after heat exchanging, at least a portion of said first effluent stream passes into said second alkylation zone wherein a $C_2$–$C_5$ olefin and an aromatic hydrocarbon react to form alkylaromatic hydrocarbons to produce said second effluent stream.

6. The process of claim 3 further characterized in that after heat exchanging, at least a portion of said first effluent stream passes into said second alkylation zone wherein a $C_2$–$C_5$ olefin and an aromatic hydrocarbon react to form alkylaromatic hydrocarbons to produce an outlet stream comprising said alkylaromatic hydrocarbons, and at least a portion of said outlet stream passes into a third separation zone to separate the entering hydrocarbons and produce an overhead stream comprising said $C_2$–$C_5$ hydrocarbons and said second effluent stream, and said overhead stream is rejected from said process.

7. A process for alkylating aromatic hydrocarbons which comprises the steps of:
   a. alkylating at least one aromatic hydrocarbon with at least one addition compound in a first alkylation zone to produce a first effluent stream comprising alkylaromatic hydrocarbons;
   b. passing a first portion of said first effluent stream into a second alkylation zone or a first separation zone and recovering therefrom a second effluent stream comprising alkylaromatic hydrocarbons and having a molecular weight that is greater than the molecular weight of said first effluent stream;
   c. flashing at least a portion of said second effluent stream;
   d. heat exchanging in a means for indirect heat exchange at least a portion of said second effluent stream after flashing;
   e. heat exchanging in said means for indirect heat exchange a second portion of said first effluent stream;
   f. recycling to said first alkylation zone at least a portion of said second portion of said first effluent stream after heat exchanging; and
   g. recovering alkylaromatic hydrocarbons in a second separation zone from at least a portion of said portion of said second effluent stream after heat exchanging.

8. The process of claim 7 further characterized in that said addition compound is a $C_2$-$C_5$ olefin.

9. The process of claim 7 further characterized in that said first effluent stream further comprises a $C_2$-$C_5$ hydrocarbon and said first portion of said first effluent stream passes into said first separation zone to separate the entering hydrocarbons and produce an overhead stream comprising said $C_2$-$C_5$ hydrocarbons and said second effluent stream, and said overhead stream is rejected from said process.

10. The process of claim 7 further characterized in that said first portion of said first effluent stream passes into said second alkylation zone wherein a $C_2$-$C_5$ olefin and an aromatic hydrocarbon react to form alkylaromatic hydrocarbons to produce said second effluent stream.

11. The process of claim 7 further characterized in that said first portion of said first effluent stream passes into said second alkylation zone wherein a $C_2$-$C_5$ olefin and an aromatic hydrocarbon react to form alkylaromatic hydrocarbons to produce an outlet stream comprising said alkylaromatic hydrocarbons, and at least a portion of said outlet stream passes into a third separation zone to separate the entering hydrocarbons and produce an overhead stream comprising said $C_2$-$C_5$ hydrocarbons and said second effluent stream, and said overhead stream is rejected from said process.

* * * * *